(12) United States Patent
Fan (10) Patent No.: US 11,849,911 B2
(45) Date of Patent: Dec. 26, 2023

(54) ULTRASONIC ECHOGENIC DEVICE

(71) Applicant: BECTON, DICKINSON AND COMPANY, Franklin Lakes, NJ (US)

(72) Inventor: Qingqing Fan, Shanghai (CN)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 0 days.

(21) Appl. No.: 18/008,217

(22) PCT Filed: Jun. 4, 2021

(86) PCT No.: PCT/US2021/035887
§ 371 (c)(1),
(2) Date: Dec. 5, 2022

(87) PCT Pub. No.: WO2021/247988
PCT Pub. Date: Dec. 9, 2021

(65) Prior Publication Data
US 2023/0190405 A1    Jun. 22, 2023

(30) Foreign Application Priority Data
Jun. 5, 2020   (CN) .......................... 202021026053.8

(51) Int. Cl.
*A61B 90/00*   (2016.01)
*A61M 25/01*   (2006.01)

(52) U.S. Cl.
CPC ......... *A61B 90/39* (2016.02); *A61M 25/0108* (2013.01); *A61B 2090/3925* (2016.02); *A61B 2090/3929* (2016.02)

(58) Field of Classification Search
CPC ....... A61M 25/0108; A61B 2090/3925; A61B 8/0841
See application file for complete search history.

(56) References Cited

U.S. PATENT DOCUMENTS

| | | |
|---|---|---|
| 5,289,831 A | 3/1994 | Bosley |
| 6,506,156 B1 | 1/2003 | Jones |
| 2004/0106891 A1 | 6/2004 | Langan |
| 2013/0053770 A1 | 2/2013 | Aggerholm |

FOREIGN PATENT DOCUMENTS

| | | |
|---|---|---|
| EP | 2644211 A2 | 10/2013 |
| EP | 3088038 A | 11/2016 |

*Primary Examiner* — Amelie R Davis
(74) *Attorney, Agent, or Firm* — Dickinson Wright PLLC; Andrew D. Dorisio (57) ABSTRACT

An ultrasonic echogenic device (100) includes a base layer (1), an echogenic layer (2) covering the base layer (1) and adhered to the base layer (1) at least by a separate lower adhesive (4), an outer layer (3) covering the echogenic layer (2) and adhered to the echogenic layer (2) at least by a separate upper adhesive (5), wherein the ultrasonic echogenic device (100) is configured such that a rough interface is provided at a position where the echogenic material of the echogenic layer (2) contacts at least the upper surface of the upper adhesive (5) and the lower adhesive (4), and the outer surface of the outer layer (3) at least partially follows an undulation of the rough interface. An ultrasonic echogenic device (100) with a simple structure and easily formed is obtained.

34 Claims, 7 Drawing Sheets

ULTRASONIC ECHOGENIC DEVICE

This application claims the benefit of Chinese Application for Utility Model No. 202021026053.8, the disclosure of which is incorporated herein by reference.

TECHNICAL FIELD

The present application also relates to an ultrasonic echogenic device. Such ultrasonic echogenic device may be included and/or formed in a balloon dilatation catheter or other polymer medical devices, for example, as an echogenic wall or an echogenic layer.

BACKGROUND OF THE INVENTION

During a medical process using an ultrasonic device and an ultrasonic detection method, a medical instrument is usually required to be visible in ultrasonic imaging, which requires that at least a portion of the medical instrument has an echogenic characteristic, that is, capable of effectively reflecting ultrasonic waves for detection, such as B-type ultrasonic waves.

The echogenic component is usually dispersed in a polymer solution or matrix, and the echogenic characteristic is mainly hindered by a surrounding polymer. As a result, the concentration of the echogenic component needs to be high to obtain a satisfactory echogenic characteristic of the final product, and such mixing or embedding increases the complexity of the structure and process, and changes the properties of the original polymer.

U.S. Pat. No. 6,506,156B1 discloses a method of forming an echogenic layer from a polymer matrix having a plurality of voids and/or glass microsphere particles. The plurality of void spaces are formed in order to dissolve a portion in the polymer matrix whilst maintaining another phase after curing. This method is inefficient since only the dissolved phase on the surface may form voids rapidly, and the components in the center of the matrix are not easily dissolved. The glass microspheres used in this art are adhered to the polymer matrix by an electrostatic adhesive force, which requires the base layer to be insulative.

US2013/0053770A1 discloses an echogenic balloon formed by two layers, wherein one layer is a polymer layer, and the other layer is a polymer having a radiopaque material of 60% to 80% by weight. Due to a high concentration of the filler, the blowing process of the second balloon wall becomes difficult, and the filler may reduce certain mechanical properties, such as flexibility and elongation, of the balloon wall.

SUMMARY

The present disclosure aims to provide an ultrasonic echogenic device and a related method thereof, in order to form a final product conveniently with a relatively simple configuration and a low amount of added echogenic material and bring a favorable echogenic characteristic to the same.

According to one aspect of the disclosure, an ultrasonic echogenic device comprises a base layer; an echogenic layer covering the base layer and adhered to the base layer at least by a separate lower adhesive; an outer layer covering the echogenic layer and adhered to the echogenic layer at least by a separate upper adhesive. The ultrasonic echogenic device is configured such that a rough interface is provided (uneven interface) at a position where the echogenic material of the echogenic layer contacts at least the upper adhesive of the upper adhesive and the lower adhesive, and the outer surface of the outer layer at least partially, and may substantially follow an undulation of the rough interface. Therefore, this is different from mixing and/or surrounding the echogenic material in the polymer. The ultrasonic echogenic device according to the present disclosure is constructed as a multilayer structure, particularly a film structure obtained by coating layer by layer, and the echogenic material is substantially only in a specific echogenic layer.

According to some embodiments, the total thickness of the outer layer and the upper adhesive is less than 20 um, such as less than 10 um, and for example less than 5um. Therefore, the outer layer and the upper adhesive may be sufficiently thin to avoid masking of rough interfaces. In other words, the upper adhesive may be as thin as possible under the premise of maintaining the adhesion, so as to avoid that the rough interface of the echogenic layer is filled up by an excessive adhesive. Moreover, it will not occur that the outer surface of the outer layer does not follow the above-described unevenness of the interface due to an excessive thickness of the outer layer.

According to some embodiments, the hardness of the outer layer and the upper adhesive is lower than the echogenic material of the echogenic layer. Therefore, the outer layer and the upper adhesive may be sufficiently soft to have a favorable compliance.

According to some embodiments, the ultrasonic echogenic device may form a planar structure, or may form a cylindrical structure.

According to some embodiments, the echogenic material of the echogenic layer is substantially not embedded in the base layer. According to some embodiments, the echogenic material of the echogenic layer is substantially not embedded in the outer layer. Therefore, the ultrasonic echogenic device is formed in a well-layered structure in a thickness direction. According to some embodiments, the echogenic material of the echogenic layer is substantially only between the interfaces with the upper adhesive and the lower adhesive. For example, at least 90%, or even 95% of the echogenic material of the echogenic layer is between the interfaces with the upper adhesive and the lower adhesive. In other words, at most 10%, or even 5% of the echogenic material of the echogenic layer is beyond the interfaces with the upper adhesive and the lower adhesive. Therefore, the multilayer structure of the ultrasonic echogenic device is substantially a configuration not nested with each other, and the boundary of the aggregation area where majority of the echogenic material of the echogenic layer is located is uneven.

According to some embodiments, the echogenic material of the echogenic layer covers 30%-100% of an extended area of the base layer. According to some embodiments, the outer layer covers at least an entire extended area of the echogenic material, such as an entire extended area of the base layer. In this way, at a position where no echogenic material is provided in the echogenic layer, the outer layer and the base layer might be directly adhered by an adhesive existed.

According to some embodiments, the echogenic material of the echogenic layer may form one or more pattern areas, such as lines, spirals, squares, spots, or combinations thereof. According to some embodiments, the smallest dimension size of the pattern area may be greater than 0.8 mm. According to some embodiments, the interval between the pattern areas may be greater than 0.5 mm. Particularly, the minimum dimension size of the pattern area and the interval between the pattern areas may be both no less than 1 mm. Therefore, the presence, position, and/or orientation of the ultrasonic echogenic device may be more easily recognized in an image.

According to some embodiments, the thickness of the echogenic layer may be less than 100 um. Here, due to the unevenness of the above-described interface, the thickness of the echogenic layer may be defined as an average thickness of the area occupied by the echogenic material of the echogenic layer.

According to some embodiments, the echogenic material of the echogenic layer may be glass beads, for example, may be selected from organic or inorganic glass beads. According to some embodiments, the glass beads may be spheres or ellipsoids (i.e., spherical or sub-spherical) with an overall dimension less than 100 um, for example between 40-50 um.

According to some embodiments, the echogenic material of the echogenic layer may be metal powder, for example, may be selected from titanium, nitinol, silver, gold, and tungsten. According to some embodiments, the particle diameter of the metal powder is between 800 mesh and 180 mesh, for example between 400 mesh and 240 mesh.

According to some embodiments, the echogenic material of the echogenic layer may be distributed in a configuration of no more than 4 sub-layers, and in the case of a non-single sub-layer, each of the sub-layers may be adhered by further adhesive. Of course, it is preferable to still maintain the thickness of the echogenic layer to be less than 100 um.

According to some embodiments, the base layer may be made from a polymer material, such as a base layer of polyethylene terephthalate (PET).

According to some embodiments, the outer layer may be made from a polymer material, such as an outer layer of polypropylene (PP) or polyetheramide (Pebax).

According to some embodiments, the adhesive may be waterborne or solvent based.

According to some embodiments, the adhesive may be thermoplastic or thermosetting.

According to some embodiments, the material type of the adhesive may be epoxy resin, acrylate, polyurethane, and polyvinyl acetal.

According to some embodiments, the adhesive may be in a single component or in two components.

According to some embodiments, the adhesive may be selected to be a pressure sensitive adhesive.

According to some embodiments, the curing or drying temperature of the adhesive does not exceed 120° C. Particularly, the adhesive may be a waterborne polyurethane pressure-sensitive adhesive.

According to some embodiments, the lower adhesive for adhesion may be pre-applied to the surface of the base layer facing the echogenic layer (i.e., an outer surface). Therefore, it is convenient to arrange the echogenic material such as the above-described glass beads or metal powder on the lower adhesive at a certain coverage ratio and/or in a certain pattern.

According to some embodiments, the upper adhesive for adhesion may be pre-applied to at least one of facing faces of the echogenic layer and the outer layer, such as to the surface of the outer layer facing the echogenic layer (i.e., an inner surface).

According to another aspect of the disclosure, a method of forming an ultrasonic echogenic device is provided. The method includes providing a base layer. The base layer may be independent or may come from a surface layer of the medical device. The method includes adhering the echogenic layer to the base layer at least using a lower adhesive. As described above, the lower adhesive for adhesion may be pre-applied to the surface of the base layer facing the echogenic layer. During adhesion of the echogenic layer, the echogenic layer may be applied to the lower adhesive in a manner having one or more of the above-described characteristics such as thickness, coverage ratio, pattern and material. The method includes adhering the outer layer to the echogenic layer at least using an upper adhesive. As described above, the upper adhesive for adhesion may be pre-applied to at least one of facing faces of the echogenic layer and the outer layer, such as to the surface of the outer layer facing the echogenic layer. The method includes forming a rough interface (uneven interface) at a position where the echogenic material of the echogenic layer contacts an adhesive, such as at least the upper adhesive of the upper adhesive and the lower adhesive, and making the outer surface of the outer layer at least partially, may substantially follow an undulation of the rough interface. According to some embodiments, the ultrasonic echogenic device may form a planar structure, or may form a cylindrical structure.

According to some embodiments, the characteristics of the base layer, the echogenic layer, the outer layer and the adhesive may be provided as described above.

According to the present disclosure, an ultrasonic echogenic device with a simple structure and easily formed is obtained. Such ultrasonic echogenic device may be applied to a plurality of medical instruments, and may even be directly formed on corresponding instruments.

According to the present ultrasonic echogenic device, a favorable ultrasonic echogenicity is obtained by adding less echogenic material. Specifically, the echogenic material (such as the above-described metal powder/glass beads) is disposed in a layered structure as a thin layer, and almost entirely distributed in the same layer (that is, aggregated distribution), and form a rough interface (for example so that the outer surface of the outer layer undulates accordingly), thereby providing an effective echogenic characteristic, and also substantially maintaining an original process/performance of the base layer.

BRIEF DESCRIPTION OF THE DRAWING FIGURES

Other features of the present application will become apparent from the following description of exemplary embodiments with reference to the accompanying drawings.

DETAILED DESCRIPTION

The present application will be described with reference to the accompanying drawings, in which certain embodiments of the present application are shown. However, the present application may be implemented in many different forms, and should not be construed as limited to the embodiments depicted and described herein. Rather, these embodiments are provided so that the present disclosure will be thorough and complete, and will adequately convey the scope of the present application to those skilled in the art. It will also be understood that the embodiments disclosed herein may be combined in any manner and/or combination so that many additional embodiments may be provided.

Unless otherwise defined, all the technical and scientific terms used in the present disclosure have the same meaning as commonly understood by those of ordinary skill in the art to which the present application belongs. The terms used in the above-described description is for the purpose of describing specific embodiments only, but not intended to limit the present application.

Unless clearly indicated in the content otherwise, as used in the present specification and the appended claims, the singular forms "a", "an" and "the" include plural referents. It should also be noted that, unless clearly indicated in the content otherwise, the term "or" is generally adopted in the sense that it includes "and/or".

For ease of description, in the accompanying drawings, like reference signs refer to like modules, units, and/or components.

The embodiments described below are only as specific examples. However, the present application is not limited to the embodiments described in the specification.

Figure 1A:
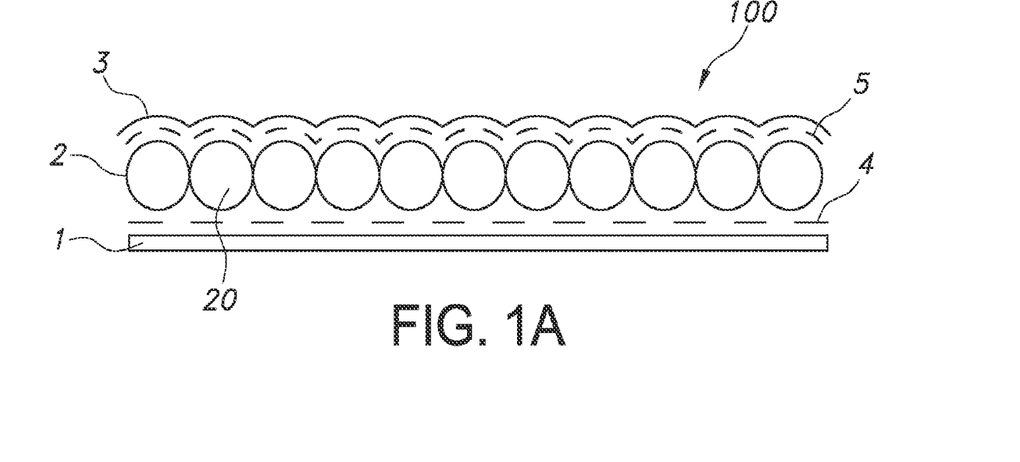
FIGS. 1A-1B schematically illustrate a portion of the ultrasonic echogenic device according to the present application.
Figure 1B:
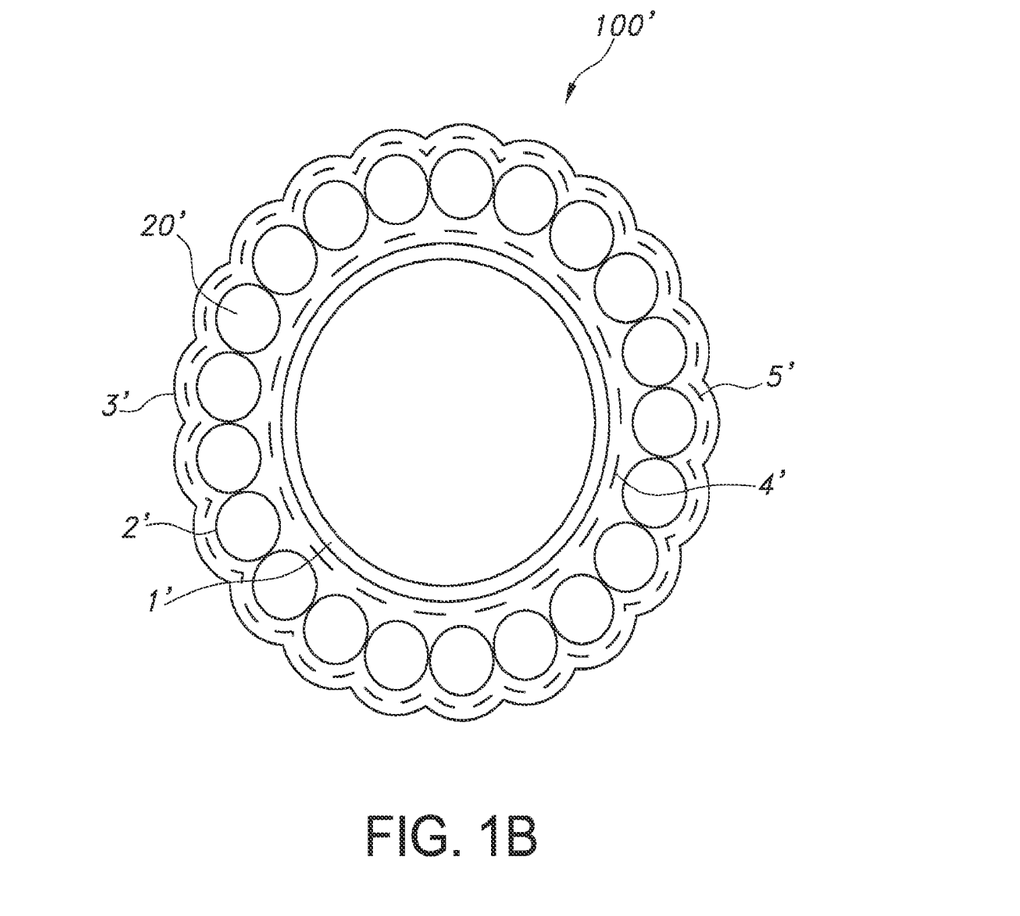

Referring to FIGS. 1A-1B, a schematic illustration of a portion of the ultrasonic echogenic device according to the present application is shown. In FIG. 1A, a portion of the ultrasonic echogenic device 100 is formed into a planar structure; in FIG. 1B, a portion of the ultrasonic echogenic device 100' is formed into a cylindrical structure.

According to the present disclosure, the ultrasonic echogenic device 100, 100' generally includes three layers: a base layer 1, 1', an echogenic layer 2, 2', and an outer layer 3, 3'. As shown, the echogenic layer 2, 2' covers the base layer 1, 1', and the echogenic layer 2, 2' is adhered to the base layer 1, 1' at least by separate lower adhesives 4, 4', the outer layer 3, 3' covers the echogenic layer 2, 2, and the outer layer 3, 3' is adhered to the echogenic layer 2, 2' at least by separate upper adhesives 5, 5'. In the present application, the ultrasonic echogenic device 100, 100' is configured such that a rough interface is provided (uneven interface) at a position where the echogenic material 20, 20' of the echogenic layer 2, 2' at least contacts the upper adhesive 5, 5' of the lower adhesive 4, 4' and the upper adhesive 5, 5' and the outer surface of the outer layer 3, 3' at least partially, may substantially follow an undulation of the rough interface.

As shown in FIGS. 1A-1B, the echogenic material 20, 20' is at different heights along a thickness direction. Here, the rough interface will extend substantially perpendicular to a thickness direction of the ultrasonic echogenic devices 100, 100', i.e., extending substantially horizontally in FIG. 1A, and extending substantially circumferentially in FIG. 1B. Although not explicitly depicted, the outer surface of the outer layer 3, 3' will also at least partially, and may substantially change as a function of the height of the echogenic material 20, 20'.

Referring now to FIGS. 2A-2D and 3A-3D, schematic illustrations of a construction of the ultrasonic echogenic device 100, 100' of FIGS. 1A-1B according to the present application are shown respectively.

Figure 2A:
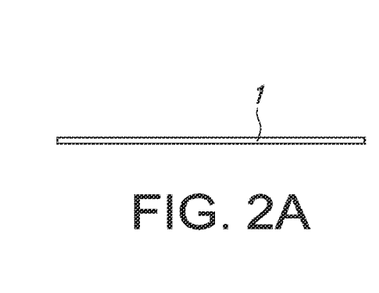
FIGS. 2A-2D schematically illustrate a construction of the ultrasonic echogenic device of FIG. 1A according to the present application.
Figure 2B:
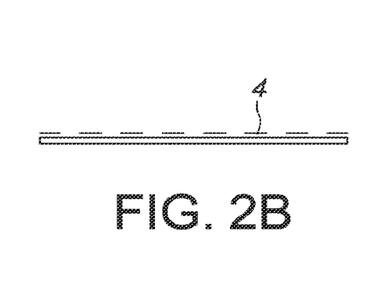
Figure 2C:
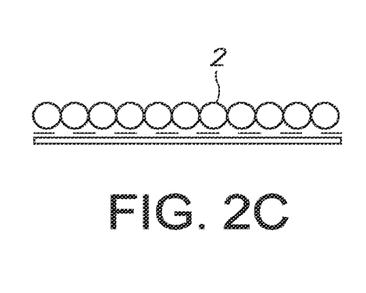
Figure 2D:
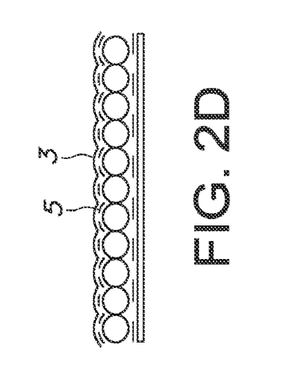
Figure 3A:
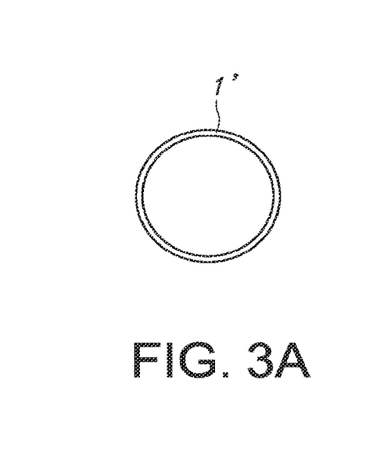
FIGS. 3A-3D schematically illustrate a construction of the ultrasonic echogenic device of FIG. 1B according to the present application.
Figure 3B:
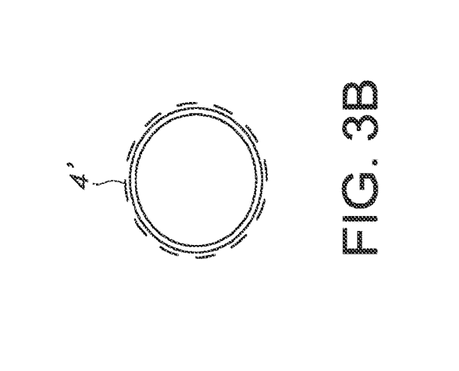
Figure 3C:
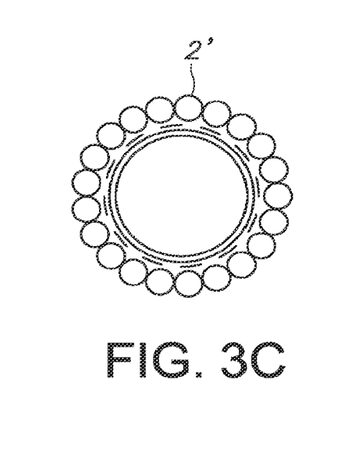
Figure 3D:
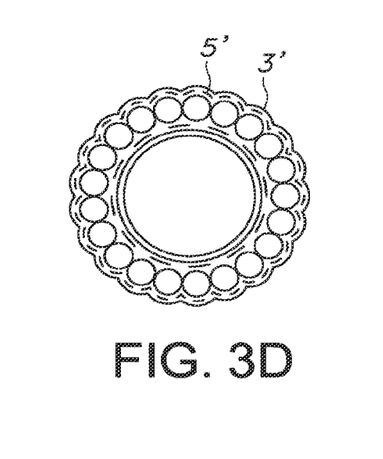

In such exemplary construction method of forming the ultrasonic echogenic device 100, 100', referring first to FIGS. 2A, 3A, the base layer 1, 1' is provided. Here, the base layer 1, 1' is shown to be separate. However, the base layer may also come from the surface layer of the medical device. Next, referring to FIGS. 2B, 3B, the lower adhesive 4, 4' is applied to the surface of the base layer facing the echogenic layer. Next, referring to 2C, 3C, the echogenic layer 2, 2' is adhered to the base layer at least using the lower adhesive. Next, referring to 2D, 3D, the outer layer 3, 3' is adhered to the echogenic layer at least using the upper adhesive 5, 5'. Before adhesion of the echogenic layer, the upper adhesive is applied to at least one of facing faces of the echogenic layer and the outer layer, and the upper adhesive is applied to the surface of the outer layer facing the echogenic layer. During a construction process, a rough interface (uneven interface) is formed at a position where the echogenic material of the echogenic layer contacts at least the upper adhesive of the upper adhesive and the lower adhesive, and the outer surface of the outer layer at least partially, substantially follows an undulation of the rough interface.

It should be noted that FIGS. 1A-3D are very schematic. In order to clarify the structure and construction of the ultrasonic echogenic devices 100, 100', the size and shape of some features are not necessarily drawn to scale and might be exaggerated.

It should be noted that the ultrasonic echogenic device according to the present application is not limited to the illustrated shape, but may take other suitable shapes not shown as necessary and may even be attached to an external surface of the medical device without departing from the spirit and scope of the present application.

According to the illustrated embodiments, the echogenic material 20, 20' of the echogenic layer 2, 2' is substantially not embedded in the base layer 1, 1', and also substantially not embedded in the outer layer 3, 3'. Therefore, the echogenic material 20, 20' of the echogenic layer 2, 2' is substantially only between the interfaces with the upper adhesive 5, 5', and the lower adhesive 4, 4'. In particular, at least 90%, or even 95% of the echogenic materials 20, 20' of the echogenic layers 2, 2' are between the interfaces with the upper adhesive 5, 5', the lower adhesive 4, 4'. In other words, at most 10%, or even 5% of the echogenic materials 20, 20' of the echogenic layer 2, 2' are beyond the interfaces with the upper adhesive 5, 5', and the lower adhesive 4, 4'.

This forms an aggregated area where majority of the echogenic material 20, 20' of the echogenic layer 2, 2' is located, wherein the boundary of the aggregated area is uneven, such as the rough interface described above, and the outer surface of the outer layer advantageously follows this rough interface. In some cases, the total thickness of the outer layer and the upper adhesive is less than 20 um, such as less than 10 um, for example less than 5um. In some cases, the hardness of the outer layer and the upper adhesive is lower than the echogenic material of the echogenic layer.

Figure 4:
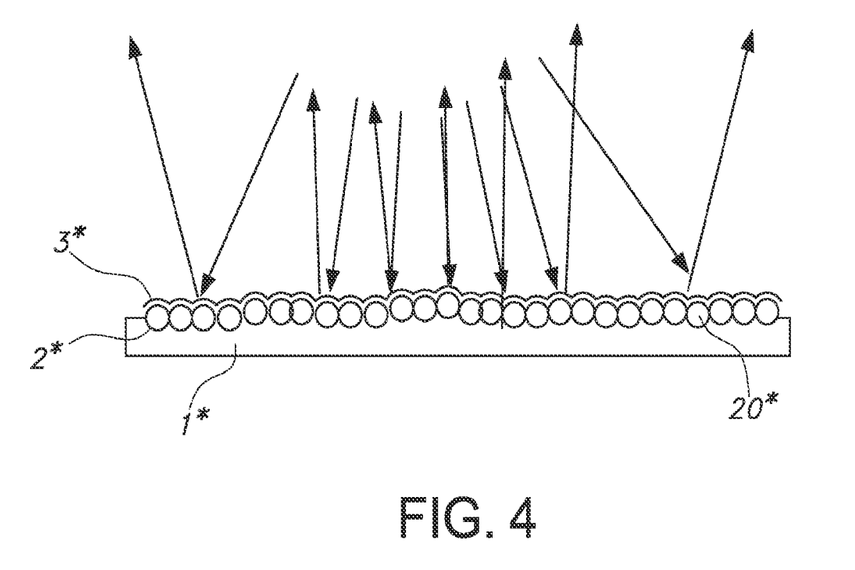
FIG. 4 schematically illustrates a principle of the ultrasonic echogenic device according to the present application.

Referring to FIG. 4, a schematic illustration of a principle of the ultrasonic echogenic device according to the present application is shown. Generally speaking, during the ultrasonic echogenic process, the ultrasonic probe receives a return sound of the ultrasonic wave emitted by itself, and converts such return sound into an electrical signal which is then displayed on the screen in a gray form. The stronger the return sound received by the probe is, the better the echogenicity of the object detected by it will be. If the ultrasonic echogenicity needs to be enhanced, it is necessary to have more return sound be received by the ultrasonic probe. As shown, when the outer surface roughness of the outer layer 3\* increases, the diffuse reflection of sound waves on the interface is increased, thereby increasing the energy returned to the ultrasonic probe. Such diffuse reflection is shown schematically above the outer layer 3\* of FIG. 4. Of course, since some sound waves might be transmitted to the rough interface of the echogenic material 20\* of the echogenic layer 2\*, the diffuse reflection may also occur here.

It should be noted that for the sake of clarity, only the base layer 1\*, the echogenic layer 2\* (the echogenic material 20\*) and the outer layer 3\* of the planar ultrasonic echogenic device are shown very schematically, and the size and shape of some features are not necessarily drawn to scale and might be exaggerated. However, the principle as described may be applied to suitable configurations without departing from the spirit and scope of the present application.

Figure 5A:
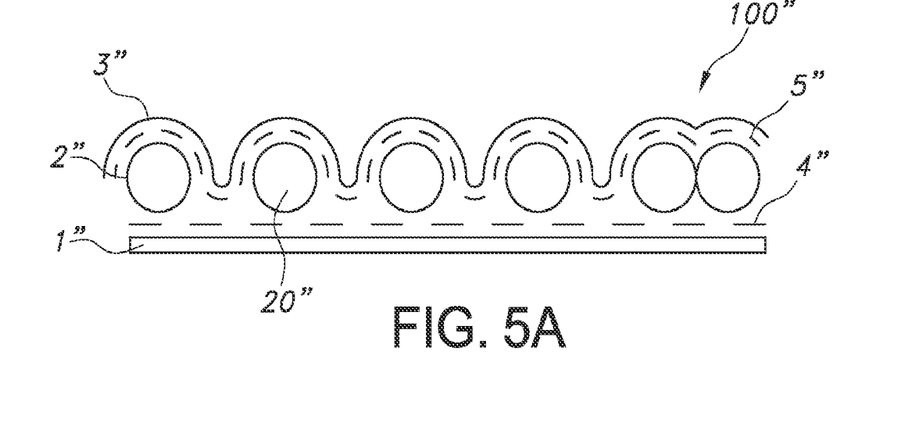
FIGS. 5A-5B schematically illustrate a portion of the ultrasonic echogenic device according to the present application.
Figure 5B:
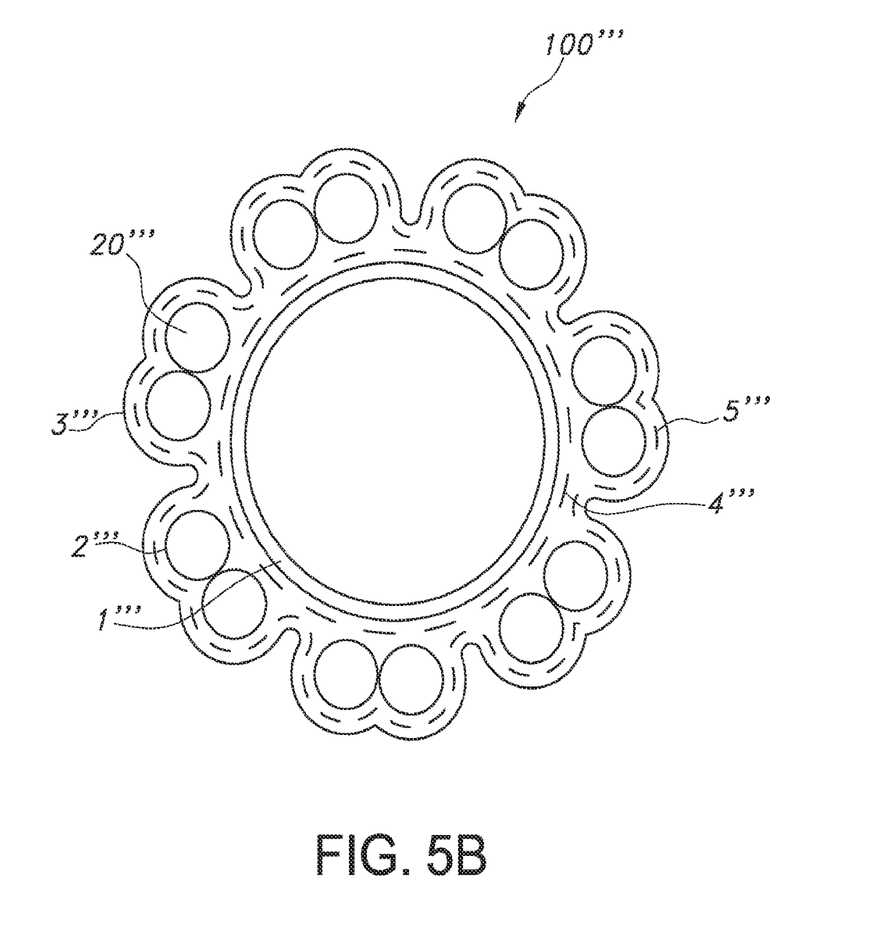

Referring to FIGS. 5A-5B, schematic illustrations of a portion of the ultrasonic echogenic device 100", 100''' according to the present application are shown. Similar to FIG. 1A, in FIG. 5A, a portion of the ultrasonic echogenic device 100" is formed into a planar structure; similar to FIG. 1B, in FIG. 5B, a portion of the ultrasonic echogenic device 100''' is formed into a cylindrical structure.

The ultrasonic echogenic devices 100", 100''' are constructed substantially similar to the ultrasonic echogenic devices 100, 100', and also include the base layer 1", 1", the echogenic layer 2", 2" and the outer layer 3", 3''' as well as the upper adhesive 5", 5''' and the lower adhesive 4", 4" for adhesion. The difference lies in the coverage ratio of the echogenic layer 2", 2', particularly of the echogenic material 20", 20'''.

In the embodiment of FIGS. 1A-1B, it may be considered that the echogenic material 20, 20' of the echogenic layer 2, 2' substantially covers 100% of an extended area of the base layer 1, 1'; while in the embodiment of FIGS. 5A-5B, it may be seen that the echogenic material 20", 20' of the echogenic layer 2", 2''' does not completely cover an extended area of the base layer 1", 1'''. In other words, the coverage ratio may be less than 100%. In some cases, coverage may be between 30% and 100%.

In the illustrated embodiment, the outer layer 3, 3', 3", 3''' cover an entire extended area of the echogenic material 20, 20', 20", 20''', and also cover an underlying extended area of the entire base layer 1, 1', 1", 1'''. In this way, at a position of the echogenic layer 2", 2''' wherein the echogenic material 20", 20''' is not provided, the outer layer 1", 1' and the base layer 1", 1''' might be adhered directly through an adhesive existed (for example, the upper adhesive 5", 5''', and the lower adhesive 4", 4"). However, in other embodiments not shown, the outer layer only covers an entire extended area of the echogenic material.

It should be noted that FIGS. 5A-5B are schematic. In order to clarify the configuration of the ultrasonic echogenic device 100", 100", the size and shape of some features are not necessarily drawn to scale and might be exaggerated.

According to the above-described and other embodiments, the thickness of the echogenic layer may be less than 100 um.

According to the above-described and other embodiments, the echogenic material of the echogenic layer may be glass beads, for example, may be selected from organic or inorganic glass beads. In some cases, the glass beads may be spheres or ellipsoids with an overall dimension of less than 100 um, such as between 40-50 um.

According to the above-described and other embodiments, the echogenic material of the echogenic layer may be metal powder, for example, may be selected from titanium, nitinol, silver, gold and tungsten. Of course, it is possible to choose other common metals or alloys that also have a favorable biocompatibility. In some cases, the particle diameter of the metal powder is between 800 mesh and 180 mesh, such as between 400 mesh and 240 mesh.

According to some embodiments, the echogenic material of the echogenic layer may be distributed in a configuration of no more than 4 sub-layers, in the case of non-single sub-layers, each of the sub-layers may be adhered therebetween by an further adhesive (e.g., an adhesive that is the same as the upper adhesive and/or the lower adhesive).

The applicant has found that, among other things, the echogenic layer formed by the echogenic material of the above-described dimensions and/or configurations can particularly prominently achieve a favorable echogenic characteristic.

It should be noted that, in FIGS. 1A-5B described above and FIGS. 7A-7D described below, for the sake of clarity, the echogenic material is drawn into a sphere with a specific larger diameter, and these spheres are distributed relative to each other and/or aggregated in a certain number to form a certain pattern. However, as mentioned above, these are merely schematic, not necessarily actual echogenic materials of the above-described dimensions and/or configurations, but rather to better describe the spirit and scope of the present disclosure.

According to the above-described and other embodiments, the base layer may be made from a polymer material, which is may be polyethylene terephthalate (PET).

According to the above-described and other embodiments, the outer layer may be made from a polymer material, which may be polypropylene (PP) or polyetheramide (Pebax).

According to the above-described and other embodiments, the adhesive may be waterborne or solvent based. In some cases, the adhesive may be thermoplastic or thermosetting. In some cases, the material type of the adhesive may be epoxy resin, acrylate, polyurethane, and polyvinyl acetal. In some cases, the adhesive may be in a single component or two components, such as in a single component. In some cases, the adhesive may be selected to be a pressure-sensitive adhesive. In some cases, the curing or drying temperature of the adhesive does not exceed 120° C. The pressure-sensitive adhesive is advantageous, which may, for example, avoid an excessive flow of the adhesive from filling up and masking the above-described uneven rough interface. The lower curing or drying temperature is advantageous, which may, for example, avoid affecting the properties of the base layer and/or the outer layer. Particularly, the adhesive may be a waterborne polyurethane pressure-sensitive adhesive.

According to the above-described and other embodiments, the lower adhesive for adhesion may be pre-applied to the surface of the base layer facing the echogenic layer (i.e., the outer surface).

According to the above-described and other embodiments, the upper adhesive for adhesion may be pre-applied to at least one of facing faces of the echogenic layer and the outer layer, such as to the surface of the outer layer facing the echogenic layer (i.e., the inner surface).

Figure 6A:
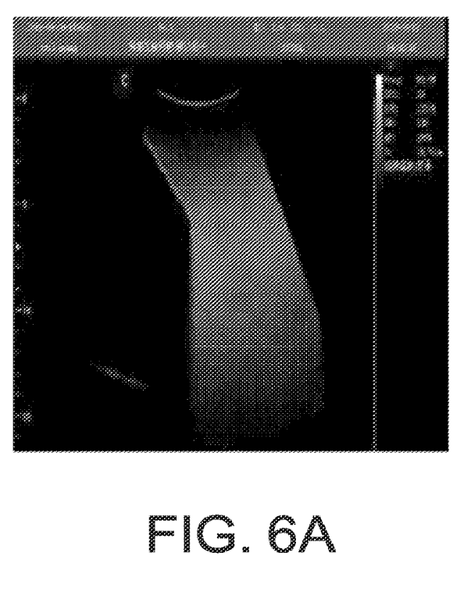
FIGS. 6A-6C compare ultrasonic images of the device according to a comparative example and a portion of the ultrasonic echogenic device according to the present application.
Figure 6B:
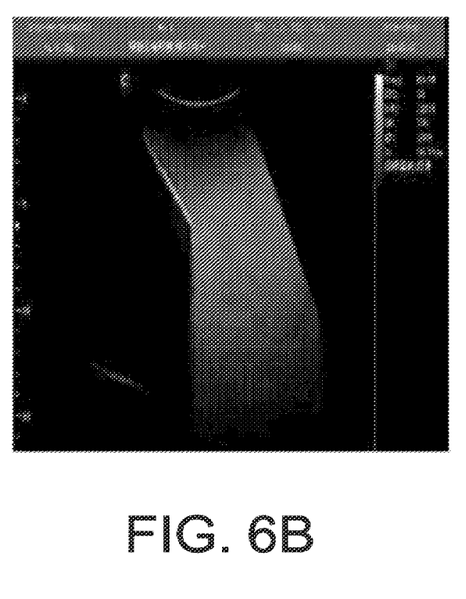
Figure 6C:
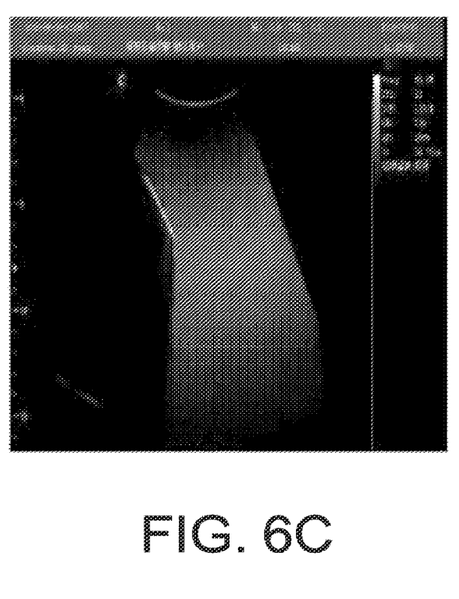

Referring now to FIGS. 6A-6C, a comparison of the ultrasonic images of the device according to a comparative example and the ultrasonic echogenic device according to the present application is shown, wherein the ultrasonic images (B-scan ultrasonic images) are obtained under the same measurement conditions and parameters.

FIG. 6A: reference example, an original polymer instrument without an additional layer.

FIG. 6B: Example 1, a cylindrical ultrasonic echogenic device with three layers: PET as the base layer; 325 mesh titanium powder as the echogenic layer adhered to the base layer using an waterborne polyurethane pressure sensitive adhesive, wherein the titanium powder is evenly distributed and covers about 70% of the entire base layer; an outer layer attached to the top using an waterborne polyurethane pressure-sensitive adhesive. The total thickness of the device is 90 μm.

FIG. 6C: example 2, a cylindrical ultrasonic echogenic device with three layers: PET as the base layer; 180-mesh glass beads as the echogenic layer adhered to the base layer using an waterborne polyurethane pressure-sensitive adhesive, wherein the glass beads are evenly distributed and cover about 90% of the entire base layer; an outer layer adhered to the top using an waterborne polyurethane pressure-sensitive adhesive. The total thickness of the device is 100 μm.

Comparing the B-scan ultrasonic images, it may be seen that compared with FIG. 6A, a portion of the samples in FIGS. 6C and 6B are whitish and the brightness is raised, which means that the echogenicity is improved. Thus it may be seen that the ultrasonic echogenic device according to the present application shows a better echogenic characteristic under a B-type ultrasonic diagnosis.

Figure 7A:
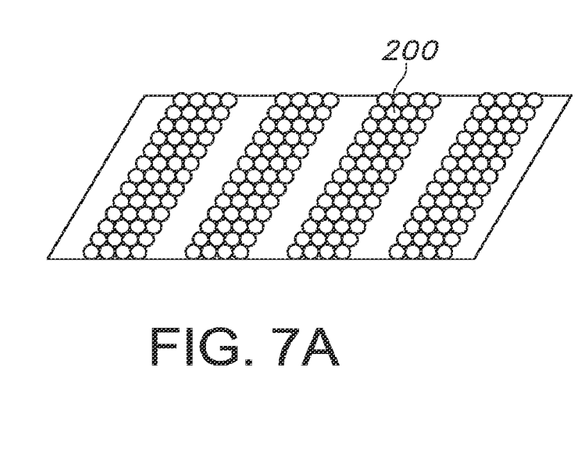
FIGS. 7A-7D schematically illustrate a portion of the ultrasonic echogenic device according to the present application.
Figure 7B:
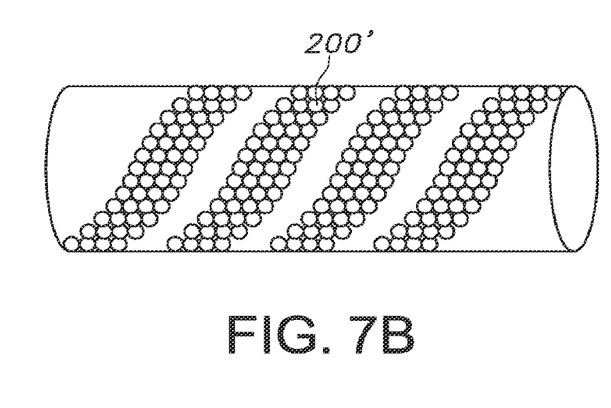
Figure 7C:
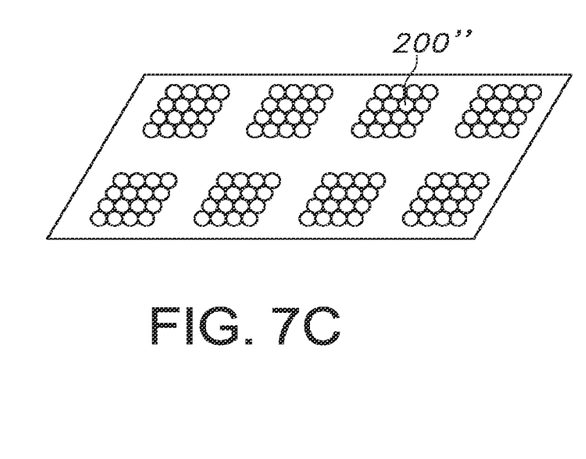
Figure 7D:
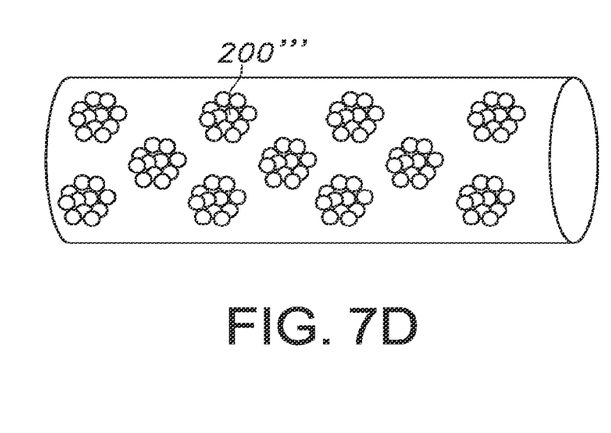

Referring to 7A-7D, schematic illustrations of a portion of the ultrasonic echogenic device according to the present application are shown. As shown, the echogenic material of the echogenic layer may also advantageously form one or more pattern areas. In FIG. 7A, the linear pattern area is formed in the ultrasonic echogenic device of a planar structure. In FIG. 7B, the spiral pattern area is formed in the ultrasonic echogenic device of a cylindrical structure. In FIG. 7C, the square-shaped pattern area is formed in the ultrasonic echogenic device of a planar structure. In FIG. 7D, the spot pattern area is formed in the ultrasonic echogenic device of a cylindrical structure.

In some cases, the minimum dimension size of the pattern area (e.g., the width of the linear portion 200 in the pattern area, the width of the spiral portion 200' in the pattern area, the minimum dimension size of the block 200'' in the pattern area, and/or the outer diameter of the spot 200''' in pattern area) may be greater than 0.8 mm, and the interval between the pattern areas (e.g., the interval between the linear portions 200 in the pattern area, the interval between the spiral portions 200' in the pattern area, the interval between the blocks 200'' in the pattern area and/or the interval between the spots 200''' in the pattern area) may be greater than 0.5 mm.

It should be noted that, for the sake of clarity, the base layer and the echogenic layer (particularly the pattern area 200-200' formed by the echogenic material) of the ultrasonic echogenic device are shown very schematically, and the dimension, shape and the like of some features are not necessarily drawn to scale and might be exaggerated. Moreover, the given pattern area 200-200' is depicted and described in a specific form in conjunction with a specific device structure. However, the ultrasonic echogenic device according to the present application is not limited to this, and each of the above-described pattern areas may have different orientations, distributions and the like without departing from the spirit and scope of the present application. Other suitable forms of pattern areas not shown are also possible. Therefore, a combination of suitable pattern areas (for example, the above-described specific form, other suitable forms, or a combination thereof) and device structures (for example, the above-described planar structure, cylindrical structure, and other suitable shapes) are provided as necessary.

Figure 8A:
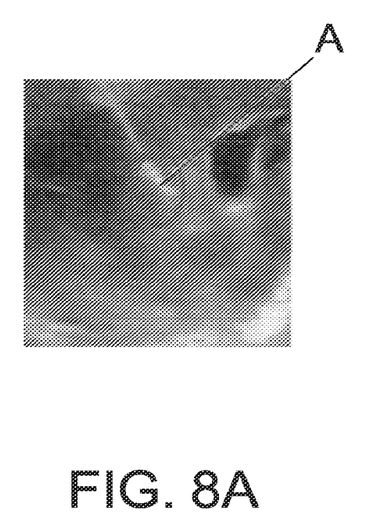
FIGS. 8A-8B are pattern recognitions of a portion of the ultrasonic echogenic device according to the present application in an ultrasonic image.
Figure 8B:
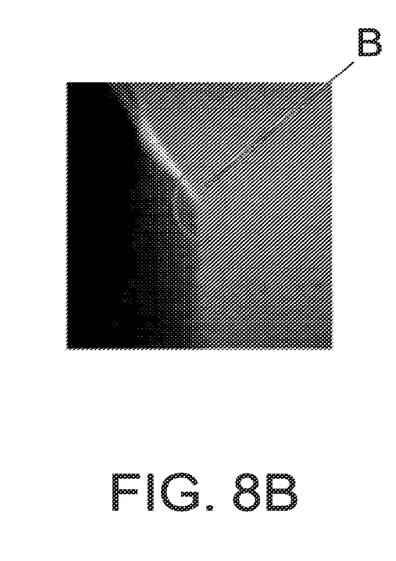

Referring to FIGS. 8A-8B, a pattern recognition of a portion of the ultrasonic echogenic device according to the present application in an ultrasonic image is shown, wherein the ultrasonic image (B-scan ultrasonic image) is obtained under the same measurement conditions and parameters.

Except for the pattern areas, the ultrasonic echogenic devices shown in FIGS. 8A-8B are substantially the same. The two ultrasonic echogenic devices tested both use linear pattern areas, but with different settings in the dimension and the interval. For the former and the latter, the width of the linear portion in the pattern areas is 1 mm and 0.8 mm respectively. Similarly, for the former and the latter, the interval between the linear portions in the pattern areas is 1 mm and 0.5 mm respectively.

Comparing the B-scan ultrasonic images, it may be seen that the lines may be roughly seen from the area B in FIG. 8B, and the lines may be clearly seen from the area A in FIG. 8A, which means an improved recognition. Thus it may be seen that it is particularly preferable that the minimum dimension size of the pattern area and the interval between the pattern areas may be both no less than 1 mm.

Thus, according to the present disclosure, the need for the echogenic characteristics may be substantially realized with a simple structure and means using the ultrasonic echogenic device and the related method.

The above which is an explanation of the present disclosure, should not be interpreted as a limitation of the present disclosure. Although exemplary embodiments of the present disclosure have been described, those skilled in the art will readily understand that many modifications may be made in the exemplary embodiments without substantively departing from the novel teachings and advantages of the present disclosure. For example, the features concerning the system and the features concerning the method may be combined in any manner to form further embodiments. Therefore, all these modifications are intended to be included within the scope of the present disclosure as defined in the claims. The present disclosure is defined by the appended claims, which include equivalent forms of the claims.

The invention claimed is:

1. An ultrasonic echogenic device, characterized in that the ultrasonic echogenic device comprises:
    a base layer;
    an echogenic layer covering the base layer, and adhered to the base layer at least by a separate lower adhesive;
    an outer layer covering the echogenic layer, and adhered to the echogenic layer at least by a separate upper adhesive;
    wherein the ultrasonic echogenic device is configured such that a rough interface is provided at a position where the echogenic material of the echogenic layer contacts at least the upper adhesive, and the outer surface of the outer layer at least partially follows an undulation of the rough interface.

2. The ultrasonic echogenic device according to claim 1, characterized in that a total thickness of the outer layer and the upper adhesive is less than 20 um.

3. The ultrasonic echogenic device according to claim 2, characterized in that a total thickness of the outer layer and the upper adhesive is less than 10 um.

4. The ultrasonic echogenic device according to claim 3, characterized in that a total thickness of the outer layer and the upper adhesive is less than 5 um.

5. The ultrasonic echogenic device according to claim 1, characterized in that a hardness of the outer layer and the upper adhesive is lower than a hardness of the echogenic material of the echogenic layer.

6. The ultrasonic echogenic device according to claim 1, characterized in that the ultrasonic echogenic device forms a planar structure or a cylindrical structure.

7. The ultrasonic echogenic device according to claim 1, wherein the echogenic material of the echogenic layer is not embedded in the base layer, and/or the echogenic material of the echogenic layer is not embedded in the outer layer.

8. The ultrasonic echogenic device according to claim 1, characterized in that at least 90% of the echogenic material of the echogenic layer is between interfaces with the upper adhesive and the lower adhesive.

9. The ultrasonic echogenic device according to claim 8, characterized in that at least 95% of the echogenic material of the echogenic layer is between interfaces with the upper adhesive and the lower adhesive.

10. The ultrasonic echogenic device according to claim 1, characterized in that the echogenic material of the echogenic layer covers 30%-100% of an extended area of the base layer.

11. The ultrasonic echogenic device according to claim 1, characterized in that the outer layer covers at least an entire extended area of the echogenic material.

12. The ultrasonic echogenic device according to claim 11, characterized in that the outer layer covers an entire extended area of the base layer.

13. The ultrasonic echogenic device according to claim 1, characterized in that the echogenic material of the echogenic layer forms one or more pattern areas.

14. The ultrasonic echogenic device according to claim 13, characterized in that the one or more pattern areas is constructed as lines, spirals, squares, spots, or a combination thereof.

15. The ultrasonic echogenic device according to claim 13, characterized in that a minimum dimension of the one or more pattern areas is larger than 0.8 mm, and/or an interval between the pattern areas is larger than 0.5 mm.

16. The ultrasonic echogenic device according to claim 15, characterized in that a minimum dimension of the one or more pattern areas and the interval between the pattern areas are both no less than 1 mm.

17. The ultrasonic echogenic device according to claim 1, characterized in that a thickness of the echogenic layer is less than 100 um.

18. The ultrasonic echogenic device according to claim 1, characterized in that the echogenic material of the echogenic layer consists in glass beads.

19. The ultrasonic echogenic device according to claim 18, characterized in that the glass beads are spheres or ellipsoids with an overall dimension of less than 100 um.

20. The ultrasonic echogenic device according to claim 18, characterized in that an overall dimension of the glass beads is between 40-50 um.

21. The ultrasonic echogenic device according to claim 1, characterized in that the echogenic material of the echogenic layer is metal powder.

22. The ultrasonic echogenic device of claim 21, characterized in that the metalpowder is selected from titanium, nitinol, silver, gold, or tungsten.

23. The ultrasonic echogenic device according to claim 21, characterized in that a particle diameter of the metal powder is between 800 mesh and 180 mesh.

24. The ultrasonic echogenic device according to claim 23, characterized in that a particle diameter of the metal powder is between 400 mesh and 240 mesh.

25. The ultrasonic echogenic device according to claim 1, characterized in that the echogenic material of the echogenic layer is distributed as a configuration of no more than 4 sub-layers, wherein each of the sub-layers is adhered therebetween by a further adhesive in the case of a non-single sub-layer.

26. The ultrasonic echogenic device according to claim 1, characterized in that the base layer includes a polymer material.

27. The ultrasonic echogenic device according to claim 26, characterized in that the polymer material comprises polyethylene terephthalate.

28. The ultrasonic echogenic device according to claim 1, characterized in that the outer layer includes a polymer material.

29. The ultrasonic echogenic device of claim 28, characterized in that the polymer material comprises polypropylene or polyetheramide.

30. The ultrasonic echogenic device according to claim 1, characterized in that the upper adhesive and the lower adhesive are a pressure-sensitive adhesive.

31. The ultrasonic echogenic device according to claim 30, characterized in that_the upper adhesive and the lower adhesive are a waterborne polyurethane pressure-sensitive adhesive.

32. The ultrasonic echogenic device of claim 1, characterized in that a curing or drying temperature of the upper adhesive and the lower adhesive do not exceed 120° C.

33. The ultrasonic echogenic device according to claim 1, characterized in that the lower adhesive is pre-applied to a surface of the base layer facing the echogenic layer.

34. The ultrasonic echogenic device according to claim 1, characterized in that the upper adhesive for adhesion is pre-applied to the surface of the outer layer facing the echogenic layer.

* * * * *

UNITED STATES PATENT AND TRADEMARK OFFICE
CERTIFICATE OF CORRECTION

PATENT NO. : 11,849,911 B2
APPLICATION NO. : 18/008217
DATED : December 26, 2023
INVENTOR(S) : Qingqing Fan It is certified that error appears in the above-identified patent and that said Letters Patent is hereby corrected as shown below:

In the Claims

Column 12, Claim 22, Line 11, please delete "metalpowder" and insert -- metal powder --.

Column 12, Claim 34, Line 52, please delete "for adhesion".

Signed and Sealed this
Twentieth Day of February, 2024

*Katherine Kelly Vidal*

Katherine Kelly Vidal
*Director of the United States Patent and Trademark Office*